United States Patent
Yang et al.

(10) Patent No.: US 10,759,708 B2
(45) Date of Patent: Sep. 1, 2020

(54) HIGH-LIGHT TRASMITTANCE ZIRCONIA SINTERED BODY, PREPARATION METHOD THEREFOR AND USE THEREOF

(71) Applicant: SHANDONG SINOCERA FUNCTIONAL MATERIAL CO., LTD., Dongying, Shandong (CN)

(72) Inventors: Aimin Yang, Shandong (CN); Xuekui Mo, Shandong (CN); Xibin Song, Shandong (CN)

(73) Assignee: Shandong Sinocera Functional Material Co., Ltd, Shandong (CN)

( * ) Notice: Subject to any disclaimer, the term of this patent is extended or adjusted under 35 U.S.C. 154(b) by 0 days.

(21) Appl. No.: 16/289,369

(22) Filed: Feb. 28, 2019

(65) Prior Publication Data

US 2019/0210927 A1 Jul. 11, 2019

Related U.S. Application Data

(63) Continuation of application No. PCT/CN2017/095747, filed on Aug. 3, 2017.

(30) Foreign Application Priority Data

Aug. 31, 2016 (CN) .......................... 2016 1 0793366

(51) Int. Cl.
| | |
|---|---|
| C04B 35/488 | (2006.01) |
| C04B 35/26 | (2006.01) |
| C04B 35/64 | (2006.01) |
| C04B 35/632 | (2006.01) |
| C01G 25/02 | (2006.01) |
| C04B 35/634 | (2006.01) |
| C04B 35/626 | (2006.01) |
| C04B 35/486 | (2006.01) |
| C04B 35/636 | (2006.01) |
| A61K 6/61 | (2020.01) |
| A61K 6/818 | (2020.01) |

(52) U.S. Cl.
CPC ............ *C04B 35/4885* (2013.01); *A61K 6/61* (2020.01); *A61K 6/818* (2020.01); *C01G 25/02* (2013.01); *C04B 35/486* (2013.01); *C04B 35/6262* (2013.01); *C04B 35/6263* (2013.01); *C04B 35/62675* (2013.01); *C04B 35/62695* (2013.01); *C04B 35/632* (2013.01); *C04B 35/6365* (2013.01); *C04B 35/63416* (2013.01); *C04B 35/63424* (2013.01); *C04B 35/63456* (2013.01); *C04B 35/63488* (2013.01); *C04B 35/64* (2013.01); *C01P 2002/52* (2013.01); *C01P 2004/51* (2013.01); *C01P 2004/61* (2013.01); *C01P 2004/62* (2013.01); *C01P 2006/12* (2013.01); *C04B 2235/3217* (2013.01); *C04B 2235/3227* (2013.01); *C04B 2235/5409* (2013.01); *C04B 2235/5445* (2013.01); *C04B 2235/668* (2013.01); *C04B 2235/96* (2013.01); *C04B 2235/9653* (2013.01); *C04B 2235/9669* (2013.01)

(58) Field of Classification Search
CPC .................................................. C04B 35/4885
See application file for complete search history.

(56) References Cited

U.S. PATENT DOCUMENTS

| | | | | |
|---|---|---|---|---|
| 9,309,157 B2* | 4/2016 | Fujisaki | ............ | A61C 13/0022 |
| 9,962,247 B2* | 5/2018 | Fujisaki | ............ | C04B 35/62695 |
| 2011/0027742 A1* | 2/2011 | Fujisaki | ................ | C04B 35/486 |
| | | | | 433/8 |
| 2014/0370453 A1* | 12/2014 | Fujisaki | ................. | C01G 25/02 |
| | | | | 433/8 |
| 2018/0134624 A1* | 5/2018 | Yang | ....................... | C04B 35/49 |

FOREIGN PATENT DOCUMENTS

| | | |
|---|---|---|
| CN | 1636932 | 7/2005 |
| CN | 101891471 | 11/2010 |
| CN | 101998939 | 3/2011 |
| CN | 102028624 | 7/2012 |
| CN | 102838348 | 12/2012 |
| CN | 104016677 | 9/2014 |
| CN | 104086175 | 10/2014 |
| CN | 106396676 | 2/2017 |
| CN | 106431395 | 2/2017 |

* cited by examiner

*Primary Examiner* — Karl E Group
(74) *Attorney, Agent, or Firm* — Levine Bagade Han LLP

(57) ABSTRACT

Provided is a high-light transmittance zirconia sintered body, prepared by processing and forming a material for the high-light transmittance zirconia sintered body, and then performing high-temperature sintering in the atmosphere under normal pressure. The material for a high-light transmittance zirconia sintered body is prepared from zirconia powder and α-aluminum oxide as raw materials, wherein the molar percentage of yttrium oxide in the zirconia powder is 4-6%. The high-light transmittance zirconia sintered body can be used for preparing a fixed dental prosthesis. The zirconia sintered body has a grain size of 0.1-0.7 μm, and due to the dispersion and toughening by aluminum oxide, the zirconia sintered body has a higher strength and toughness. Pores in the zirconia powder can be eliminated by adding aluminum oxide. The zirconia sintered body has a higher light transmittance, and the prepared dentures are good in texture, good in jade-like appearance, and closer to the human teeth.

10 Claims, No Drawings

HIGH-LIGHT TRASMITTANCE ZIRCONIA SINTERED BODY, PREPARATION METHOD THEREFOR AND USE THEREOF

CROSS-REFERENCE TO RELATED APPLICATION

This application is a continuation of International Application No. PCT/CN2017/095747, filed Aug. 3, 2017, which claims the priority to Chinese patent Application No. 201610793366.8, filed on Aug. 31, 2016, both of which are incorporated by reference herein in their entireties.

TECHNICAL FIELD

The present invention relates to the field of material engineering, specifically, to a high-light transmittance zirconia sintered body and preparation method therefor and use thereof.

BACKGROUND ART

Zirconia ceramic is a new type of biomaterial with good biocompatibility and excellent mechanical properties, which has become the focus of dental ceramic development.

CN104016677A discloses a light-transmissive zirconia sintered body and preparation method therefor. The zirconia for dental use prepared by the method has a relatively low transmittance, poor overall texture and jade-like appearance, is not aesthetically pleasing, and has certain limitations in application. ZL201010604330.3 discloses a dental high-transmittance zirconia material and preparation process thereof, which adopts a dry mixing process to prepare zirconia, prone to cause uneven distribution of strength and low strength of zirconia, and the ceramic sintered body is prone to cracking when applied.

SUMMARY OF THE INVENTION

One purpose of the present invention is to provide a novel high-light transmittance zirconia sintered body and preparation method therefor.

Another purpose of the present invention is to provide use of the high-light transmittance zirconia sintered body in the preparation of a fixed dental prosthesis.

In order to achieve the purpose of the present invention, the present invention first provides a material for a high-light transmittance zirconia sintered body, and the material is prepared by the following method: adding an appropriate amount of water to zirconia powder and grinding, during which α-aluminum oxide powder is added, then spray granulating to obtain a powder material having an average particle diameter of 0.1 μm to 0.4 μm.

The molar percentage of yttrium oxide in the zirconia powder is 4% to 6%.

The α-aluminum oxide powder has a BET specific surface area of 5 to 16 $m^2/g$.

The zirconia powder has a BET specific surface area of 8 to 16 $m^2/g$, and an average particle diameter of 0.1 to 0.4 μm.

The preparation method of the zirconia powder is as follows:

S1, a soluble zirconium salt and a soluble yttrium salt are mixed at a ratio and dissolved in water, and ammonia water is slowly added under stirring to adjust the pH of the slurry to 8 to 10;

S2, the above slurry is transferred to a reaction kettle, and hydrothermal synthesis is performed at 140 to 200° C. for 10 to 72 h;

S3, the resultant reaction solution is washed with water and dried to obtain a powder;

S4, the powder is subjected to heat treatment at 800 to 1200° C. for 2 to 5 h, and then grinding and dispersing; and S5, the dispersed particles are granulated to obtain a powder for a high-light transmittance zirconia sintered body;

In step S1, the soluble zirconium salt includes zirconium oxychloride, zirconium nitrate, zirconium sulfate and the like; and the soluble yttrium salt includes yttrium chloride, yttrium nitrate, yttrium sulfate and the like. The molar ratio of the soluble zirconium salt to the yttrium salt is 94 to 96:4 to 6, preferably 95:5.

When preparing the material, a step of adding a dispersant and a binder to the mixture of the zirconia and the α-aluminum oxide is also included.

The dispersant includes at least one selected from acrylic acid, polyacrylic acid, acrylamide, polyurethane and the like. The binder includes at least one selected from polyvinyl alcohol, polyethylene glycol, acrylic resin, carboxymethyl cellulose and the like.

The weight parts of the feedstocks for preparing the material for the high-light transmittance zirconia sintered body of the present invention are as follows: 50 to 100 parts of zirconia powder, 0.01 to 0.1 parts of α-aluminum oxide powder, 0.1 to 0.5 parts of dispersant, 0.1 to 8.0 parts of binder, and 50 to 100 parts of water.

Preferably, the weight parts of the feedstocks are as follows: 100 parts of zirconia powder, 0.1 parts of α-aluminum oxide powder, 0.2 parts of dispersant, 5 parts of binder, and 100 parts of water.

The material for the high-light transmittance zirconia sintered body of the present invention can be prepared by the following method: adding an appropriate amount of water to zirconia powder and grinding, during which α-aluminum oxide powder, water and alumina slurry are added and stirred for 5 to 30 minutes, then spray granulating to obtain a powder material having an average particle diameter of 0.1 μm to 0.4 μm for preparing a high-light transmittance zirconia sintered body.

The present invention also provides a high-light transmittance zirconia sintered body prepared from the material. A ceramic with 1 mm thick of the sintered body has a linear transmittance of >47% and a three-point bending strength of >600 MPa. The obtained sintered body has a grain size of 0.1 to 0.7 μm, and a good toughness due to the dispersion and toughening by alumina. After the sintered body is aged at 140° C. for 20 h, the monoclinic phase of the aged sintered body is <10%, and the anti-aging property is excellent.

The high-light transmittance zirconia sintered body of the present invention can be prepared by the following method: the material for a high-light transmittance zirconia sintered body is processed and molded, and then subjected to high-temperature sintering in the atmosphere under normal pressure. For example, the temperature for high-temperature sintering is maintained at 1400 to 1550° C. for 1 to 4 h.

The present invention also provides the use of the high-light transmittance zirconia sintered body in the preparation of a fixed dental prosthesis (including a denture).

The present invention further provides a fixed dental prosthesis, such as zirconia denture, prepared from the high-light transmittance zirconia sintered body.

The zirconia sintered body provided by the present invention has a grain size of 0.1 to 0.7 μm, and the zirconia sintered body has a higher strength and toughness due to the dispersion and toughening by aluminum oxide. Pores in the zirconia powder can be eliminated by adding aluminum oxide. The zirconia sintered body has a higher light transmittance, and the prepared dentures have good texture, good jade-like appearance, and are closer to the human teeth.

SPECIFIC MODES FOR CARRYING OUT THE EMBODIMENTS

The following Examples are intended to illustrate the present invention, but are not intended to limit the scope of the present invention. Unless otherwise specified, the technical means used in the examples are conventional means well known to those skilled in the art, and the raw materials used are all commercially available products.

The percent sign "%" involved in the present invention means a percentage by mass unless otherwise specified. However, the percentage of a solution, unless otherwise specified, means the number of grams of the solute contained in 100 mL solution.

The α-aluminum oxide powder used in the following Examples has a BET specific surface area of 5 to 16 $m^2/g$.

Examples 1 to 5: Material for a High-Light Transmittance Zirconia Sintered Body The material for the high-light transmittance zirconia sintered body of the present invention can be prepared by the following method: adding an appropriate amount of water to zirconia powder and grinding, during which α-aluminum oxide powder is added, and then the powder material having an average particle diameter of 0.1 to 0.4 μm for preparing the high-light transmittance zirconia sintered body was obtained by spray granulation. (Table 1)

TABLE 1

Powder for the high-light transmittance zirconia sintered body

| | Example 1 | Example 2 | Example 3 | Example 4 | Example 5 |
|---|---|---|---|---|---|
| Molar percentage of yttrium oxide in zirconia powder | 4.5 | 5.3 | 6 | 5 | 5 |
| BET specific surface area of zirconia powder, $m^2/g$ | 10-16 | 10-16 | 10-16 | 10-16 | 10-16 |
| Average particle diameter of zirconia powder, μm | 0.1-0.4 | 0.1-0.4 | 0.1-0.4 | 0.1-0.4 | 0.1-0.4 |
| Dispersant | Acrylic acid | Polyacrylic acid | Polyacrylic acid | Acrylamide | Polyurethane |
| Binder | PEG 1000 | PVA124 | PVA205 | PEG400 | PVA105 |
| Weight ratio of zirconia powder, α-aluminium oxide powder, dispersant, binder and water | 100:0.1:0.4:2:80 | 50:0.05:0.1:0.5:100 | 100:0.1:0.2:5:100 | 100:0.1:0.3:8:80 | 100:0:0.5:3:50 |
| Average particle diameter of the material for the high-light transmittance zirconia sintered body, μm | 0.210 | 0.198 | 0.202 | 0.321 | 0.189 |

The preparation method of the zirconia powder was as follows:

S1, the soluble zirconium salt (zirconium nitrate) and the soluble yttrium salt (yttrium nitrate) were mixed according to a ratio and dissolved in water, ammonia water was slowly added under stirring, and the pH of the slurry was adjusted to 8 to 10 with ammonia water;

S2, the slurry was transferred to a reaction kettle, and subjected to hydrothermal synthesis at 140 to 200° C. for 10 to 72 h;

S3, the resultant reaction solution was washed with water and dried to obtain a powder;

S4, the powder was subjected to heat treatment at 800 to 1200° C. for 2 to 5 h, and then grinding and dispersing; and S5, the dispersed particles were granulated to obtain a powder for a high-light transmittance zirconia sintered body.

Examples 6 to 10: High-Light Transmittance Zirconia Sintered Body and Preparation Method Therefor The powder prepared in Examples 1 to 5 was subjected to dry-pressing molding (molding pressure: 150 to 250 MPa), and then sintering at 1400 to 1550° C. in the atmosphere under normal pressure for 1 to 4 h to obtain the high-light transmittance zirconia sintered body. The various indexes of the obtained sintered body products were shown in Table 2.

TABLE 2

Indexes of high-light transmittance zirconia sintered body products

| | Example 6 | Example 7 | Example 8 | Example 9 | Example 10 |
|---|---|---|---|---|---|
| Linear transmittance of 1 mm thick ceramic, % | 47 | 50 | 48 | 47 | 49 |
| Three-point bending strength, MPa | 750 | 820 | 648 | 800 | 748 |
| Monoclinic phase of the aged sintered body, % | 7.6 | 5.3 | 1.2 | 2.5 | 2.8 |
| Fracture toughness, MPa · m$^{1/2}$ | 7 | 9 | 8 | 6 | 6 |

The high-light transmittance zirconia sintered body provided in the present invention can be used as dental materials such as fixed dental prostheses, for example, dentures.

Although the present invention is described in detail with general description and specific embodiments as above, it will be apparent to a person skilled in the art that some modifications and improvements can be made on the basis of the present invention. Therefore, such modifications or improvements without departing from the spirit of the present invention are intended to be within the scope of protection of the present invention.

INDUSTRIAL APPLICABILITY

The zirconia sintered body provided in the present invention has a grain size of 0.1 to 0.7 μm, and due to the dispersion and toughening by aluminum oxide, the zirconia sintered body has a higher strength and toughness. Pores in the zirconia powder can be eliminated by adding aluminum oxide. The zirconia sintered body has a higher light transmittance, and the prepared dentures have good texture, good jade-like appearance, and are closer to the human teeth.

What is claimed is:

1. A method for preparing a material for a high-light transmittance zirconia sintered body, comprising:
   adding an appropriate amount of water to zirconia powder and grinding, during which α-aluminum oxide powder is added, then spray granulating to obtain a powder material having an average particle diameter of 0.1 μm to 0.4 μm;
   wherein the molar percentage of yttrium oxide in the zirconia powder is 4% to 6%.

2. The method of claim 1, wherein the zirconia powder has a BET specific surface area of 8 to 16 m$^2$/g, and an average particle diameter of 0.1 to 0.4 μm; and wherein the method further comprises preparing the zirconia powder comprising:
   mixing a soluble zirconium salt and a soluble yttrium salt at a ratio and dissolving in water to form a slurry, and wherein pH of the slurry is adjusted to 8 to 10 with ammonia water while stirring, where the molar ratio of the soluble zirconium salt to the soluble yttrium salt during the mixing is 94 to 96:4 to 6;
   subjecting the slurry to hydrothermal synthesis at 140 to 200° C. for 10 hours to 72 hours;
   washing a resultant reaction solution with water and drying to obtain a powder;
   heat treating the powder at 800 to 1200° C. for 2 hours to 5 hours, and then grinding and dispersing; and
   granulating dispersed particles to obtain a powder for a high-light transmittance zirconia sintered body.

3. The method of claim 2, wherein the molar ratio of the soluble zirconium salt to the soluble yttrium salt during the mixing is 95:5.

4. The method of claim 3, wherein the α-aluminum oxide powder has a BET specific surface area of 5 to 16 m$^2$/g.

5. The method of claim 1, wherein the α-aluminum oxide powder has a BET specific surface area of 5 to 16 m$^2$/g.

6. The method of claim 2, wherein the α-aluminum oxide powder has a BET specific surface area of 5 to 16 m$^2$/g.

7. The method of claim 1, further comprising adding a dispersant and a binder to a mixture of the zirconia and the α-aluminum oxide;
   wherein the dispersant includes at least one selected from acrylic acid, polyacrylic acid, acrylamide, and polyurethane; and
   wherein the binder includes at least one selected from polyvinyl alcohol, polyethylene glycol, acrylic resin, and carboxymethyl cellulose.

8. The method of claim 7, wherein weight parts of the feedstocks for preparing the material are as follows: 50 to 100 parts of zirconia powder, 0.01 to 0.1 parts of α-aluminum oxide powder, 0.1 to 0.5 parts of dispersant, 0.1 to 8.0 parts of binder, and 50 to 100 parts of water.

9. The method of claim 2, further comprising adding a dispersant and a binder to a mixture of the zirconia and the α-aluminum oxide;
   wherein the dispersant includes at least one selected from acrylic acid, polyacrylic acid, acrylamide, and polyurethane; and
   wherein the binder includes at least one selected from polyvinyl alcohol, polyethylene glycol, acrylic resin, and carboxymethyl cellulose.

10. The method of claim 3, further comprising adding a dispersant and a binder to a mixture of the zirconia and the α-aluminum oxide;
    wherein the dispersant includes at least one selected from acrylic acid, polyacrylic acid, acrylamide, and polyurethane; and
    wherein the binder includes at least one selected from polyvinyl alcohol, polyethylene glycol, acrylic resin, and carboxymethyl cellulose.

* * * * *